(12) United States Patent
Masuda et al.

(10) Patent No.: US 9,453,006 B2
(45) Date of Patent: *Sep. 27, 2016

(54) CRYSTALLINE FORM HAVING SPECIFIC CRYSTAL HABIT AND PHARMACEUTICAL COMPOSITION CONTAINING THIS CRYSTALLINE FORM AS ACTIVE INGREDIENT

(71) Applicants: POLA PHARMA INC., Tokyo (JP); NIHON NOHYAKU CO., LTD., Tokyo (JP)

(72) Inventors: Takaaki Masuda, Kanagawa (JP); Yoshiyuki Miyata, Tokyo (JP); Hideo Kaneda, Tokyo (JP)

(73) Assignees: POLA PHARMA INC., Tokyo (JP); NIHON NOHYAKU CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/388,218

(22) PCT Filed: Jun. 24, 2013

(86) PCT No.: PCT/JP2013/067952
§ 371 (c)(1),
(2) Date: Sep. 25, 2014

(87) PCT Pub. No.: WO2014/136282
PCT Pub. Date: Sep. 12, 2014

(65) Prior Publication Data
US 2015/0368233 A1      Dec. 24, 2015

(30) Foreign Application Priority Data
Mar. 8, 2013 (JP) ................................. 2013-046593

(51) Int. Cl.
*C07D 409/06*          (2006.01)
(52) U.S. Cl.
CPC .................................. *C07D 409/06* (2013.01)
(58) Field of Classification Search
None
See application file for complete search history.

(56) References Cited

U.S. PATENT DOCUMENTS

| | | | | |
|---|---|---|---|---|
| 4,812,465 A * | 3/1989 | Schermanz | .......... | C07D 231/12 514/340 |
| 5,900,488 A | 5/1999 | Kodama et al. | | |
| 6,143,795 A * | 11/2000 | Moschner | ............ | A61K 9/0019 514/656 |
| 7,527,811 B2 * | 5/2009 | John | .......... | A61K 8/97 424/410 |
| 2009/0030059 A1 | 1/2009 | Miki et al. | | |
| 2009/0076109 A1 | 3/2009 | Miki et al. | | |
| 2009/0137651 A1 | 5/2009 | Kobayashi et al. | | |
| 2010/0168200 A1 | 7/2010 | Masuda et al. | | |
| 2010/0173965 A1 | 7/2010 | Masuda et al. | | |
| 2010/0204293 A1 | 8/2010 | Masuda et al. | | |
| 2010/0210702 A1 | 8/2010 | Vontz et al. | | |

(Continued)

FOREIGN PATENT DOCUMENTS

| | | | |
|---|---|---|---|
| CN | 103012385 A | * | 4/2013 |
| EP | 0715856 A1 | | 6/1996 |

(Continued)

OTHER PUBLICATIONS

An English translation of CN 103012385 A, 2013.*
U.S. Appl. No. 14/263,293, Masuda et al.
Byrn et al, "Pharmaceutical Solids: A Strategic Approach to Regulatory Considerations," *Pharmaceutical Research*, vol. 12(7), pp. 945-954 (1995).
Caira, "Crystalline Polymorphism of Organic Compounds," *Topics in Current Chemistry*, vol. 198, pp. 163-208 (1998).
International Search Report and the Written Opinion of the International Searching Authority for International Application No. PCT/JP2013/067952, mailed on Dec. 10, 2013.

(Continued)

*Primary Examiner* — Laura L. Stockton
(74) *Attorney, Agent, or Firm* — Knobbe, Martens, Olson & Bear, LLP (57) ABSTRACT

Means for improving the solubility of luliconazole is provided. A crystal of luliconazole represented by the following formula is provided, wherein the crystal has such a crystal habit that (011) plane is a specific crystal growth plane. The crystal is characterized in that $I_{(011)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than 25%, provided that integrated intensities of diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35° in a powder X-ray diffractometry using CuKα radiation.

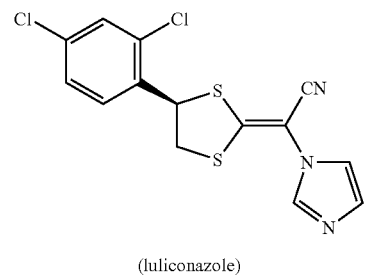

(luliconazole)

7 Claims, 2 Drawing Sheets

(56) References Cited

U.S. PATENT DOCUMENTS

| | | |
|---|---|---|
| 2010/0249202 A1 | 9/2010 | Koga et al. |
| 2012/0014893 A1 | 1/2012 | Kobayashi et al. |
| 2012/0015997 A1 | 1/2012 | Miki et al. |
| 2012/0022120 A1 | 1/2012 | Kobayashi et al. |
| 2012/0149745 A1 | 6/2012 | Kobayashi et al. |
| 2012/0329845 A1 | 12/2012 | Masuda et al. |
| 2013/0011351 A2 | 1/2013 | Kobayashi et al. |
| 2013/0090365 A1 | 4/2013 | Kubota et al. |
| 2013/0096187 A1 | 4/2013 | Kobayashi et al. |
| 2014/0080882 A1 | 3/2014 | Masuda et al. |
| 2015/0183766 A1* | 7/2015 | Masuda ............... C07D 409/06 514/397 |

FOREIGN PATENT DOCUMENTS

| | | |
|---|---|---|
| EP | 2005958 A1 | 12/2008 |
| JP | 09-100279 A | 4/1997 |
| JP | 2002-114680 A | 4/2002 |
| WO | WO 2007/102241 | 9/2007 |
| WO | WO 2007/102242 | 9/2007 |
| WO | WO 2007/102243 | 9/2007 |
| WO | WO 2009/031642 | 3/2009 |
| WO | WO 2009/031643 | 3/2009 |
| WO | WO 2009/031644 | 3/2009 |
| WO | WO 2010/117089 | 10/2010 |
| WO | WO 2010/117091 | 10/2010 |
| WO | WO 2014/041708 A1 | 3/2014 |
| WO | WO 2014/041825 A1 | 3/2014 |
| WO | WO 2014/041846 A1 | 3/2014 |
| WO | WO 2014/042043 A1 | 3/2014 |
| WO | WO 2014/115487 A1 | 7/2014 |
| WO | WO 2014/115488 A1 | 7/2014 |
| WO | WO 2014/185542 A1 | 11/2014 |

OTHER PUBLICATIONS

Niwano et al, "Efficacy of NND-502, a novel imidazole antimycotic agent, in experimental models of Candida albicans and Aspergillus fumigatus infections," *International Journal of Antimicrobial Agents*, vol. 12, pp. 221-228 (1999).

Office Action issued in corresponding Japanese Patent Application No. 2013-046593 on Mar. 25, 2014, with verified English translation.

Uchida et al, "In vitro antifungal activity of luliconazole (NND-502), a novel imidazole antifungal agent," *Journal of Infection and Chemotherapy*, vol. 10(4), pp. 216-219 (2004).

U.S. Appl. No. 14/419,864, Masuda et al.
U.S. Appl. No. 14/427,890, Masuda et al.
U.S. Appl. No. 14/592,695, Masuda et al.

* cited by examiner

CRYSTALLINE FORM HAVING SPECIFIC CRYSTAL HABIT AND PHARMACEUTICAL COMPOSITION CONTAINING THIS CRYSTALLINE FORM AS ACTIVE INGREDIENT

CROSS-REFERENCE TO RELATED APPLICATIONS

This application is the U.S. National Phase under 35 U.S.C. §371 of International Application PCT/JP2013/067952, filed Jun. 24, 2013, which claims priority to JP 2013-046593, filed Mar. 8, 2013.

TECHNICAL FIELD

The present invention relates to a crystal having a crystal habit of luliconazole which is useful as an active pharmaceutical ingredient, and a pharmaceutical composition which contains the crystal as the active pharmaceutical ingredient.

BACKGROUND ART

Luliconazole is an antifungal agent which is excellent in the action on fungi. At present, luliconazole is widely used as a pharmaceutical or medicine for *tinea pedis* and *tinea corporis*, and it is going to be applied for the action on *tinea unguium*. In relation to the pharmaceutical preparation (medicament preparation) of luliconazole, it is known as problems which should be solved, for example, that luliconazole is converted to the stereoisomers such as the SE isomer and the Z isomer, and the crystallization of luliconazole is caused immediately after the application (see, for example, Patent Documents 1 to 6). The problem of dissolution characteristics possessed by luliconazole exists on the background of the problem of the crystallization caused immediately after the application as described above, for which a lot of researches or studies have been made to realize pharmaceutical preparations (medicament preparations). However, not a few formulations have been rejected or unaccepted on account of the problem of crystallization caused during the long-term storage of the pharmaceutical preparation system. The crystallization in the system is a topic concerning the effective concentration, and hence it is affirmed that the crystal precipitation in the system is one of the important problems.

Further, it is also expected that luliconazole is to be applied to pneumonia and vaginitis (colpitis), without being limited to *Trichophyton*, because luliconazole has a strong antifungal action. In particular, as for these diseases, luliconazole also has an antiprotozoal effect on *Trichomonas* which may coexist highly probably. Therefore, it is affirmed that luliconazole is desired to be applied thereto as compared with any other antifungal agent. As for the diseases as described above, the oral administration or the administration by injection is usually adopted as the administration route thereof. In the case of the administration by injection, the problem of solubilization (solubility) solemnly exists. In other words, it is affirmed that any means to improve the solubility of luliconazole has been desired to be developed.

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/031642;
Patent Document 5: WO2009/031643;
Patent Document 6: WO2009/031644.

SUMMARY OF THE INVENTION

Technical Problem

The present invention has been made in the circumstances as described above, an object of which is to provide means for improving the solubility of luliconazole.

Solution to Problem

Taking the foregoing circumstances into consideration, the present inventors have repeatedly performed diligent researches and efforts in order to seek for any means for improving the solubility of luliconazole. As a result, it has been found out that a crystal, which has such a crystal habit that the (011) plane is a specific crystal growth plane, is obtained by recrystallizing luliconazole while being gently stirred in alcohol such as ethanol or the like which may contain water, that the crystal has an excellent affinity for solvent, and that the solubility of luliconazole is improved by preparing a solution by using the crystal. Thus, the invention has been completed. In this context, the phrase "excellent in solubility", which is referred to in the present invention, does not mean such a state that the state seems to be a solubilized state by being viewed by naked eyes but fine or minute crystals, which cannot be sensed by naked eyes, are present in a dispersed manner, but the phrase means such a state that any crystal, which may be lost by filtration, is absent even when the filtration is performed by using a filter having a pore size of 0.2 to 0.4 µm.

Specifically, the present invention has the following features.

(1) A crystal of luliconazole represented by the following formula, wherein the crystal has such a crystal habit that (011) plane is a specific crystal growth plane:

(luliconazole)

(2) The crystal as defined in (1), wherein $I_{(011)}$ with respect to a sum total of $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ is not less than 25%, provided that integrated intensities of diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10\text{-}1)}$, $I_{(011)}$, $I_{(110)}$, $I_{(11\text{-}1)}$, $I_{(10\text{-}2)}$, $I_{(11\text{-}2)}$, $I_{(020)}$, $I_{(021)}$, $I_{(20\text{-}2)}$, $I_{(121)}$, $I_{(013)}$, $I_{(11\text{-}3)}$, and $I_{(221)}$ respectively in relation to the diffraction peaks detected in a range of 2θ=5 to 35° in a powder X-ray diffractometry using CuKα radiation.

(3) The crystal as defined in (1) or (2), wherein the crystal has a monoclinic crystal system.

(4) The crystal as defined in any one of (1) to (3), wherein the crystal is recrystallized from alcohol which may contain water.

(5) A crystal of luliconazole having such a crystal habit that sulfur atom is arranged on a specific crystal growth plane.

(6) An active pharmaceutical ingredient, containing the crystal as defined in any one of (1) to (5).

(7) A method for producing a pharmaceutical composition, comprising a step of dissolving, in a solvent, the crystal as defined in any one of (1) to (5) or the active pharmaceutical ingredient as defined in (6), followed by being filtrated through a sterilizing filter (sterilization filter).

(8) The method as defined in (7), wherein the sterilizing filter is a filter which has a pore size of 0.2 μm to 0.5 μm.

(9) A pharmaceutical composition produced by the production method as defined in (7) or (8).

(10) The pharmaceutical composition as defined in (9), wherein the pharmaceutical composition is a pharmaceutical composition which is usable for vaginitis or pneumonia.

Advantageous Effects of Invention

According to the present invention, it is possible to provide means for improving the solubility of luliconazole.

DESCRIPTION OF EMBODIMENTS (1) Crystal of Luliconazole of the Present Invention

The crystal of luliconazole of the present invention is characterized in that the crystal has such a crystal habit that (011) plane is a specific crystal growth plane. The crystal having the crystal habit as described above can be prepared by dissolving luliconazole in lower alcohol such as ethanol or the like while being heated (dissolving temperature: 60 to 70° C.), performing cooling while applying gentle stirring, adding a poor solvent such as water or the like, depositing crystals, separating the crystals by means of filtration, and drying the crystals while performing blowing at a low temperature of 30 to 40° C. In this procedure, it is preferable that the amount of the poor solvent to be added is a volume of 10 to 40% with respect to the lower alcohol, for the following reason. That is, even when the amount of the poor solvent is either large or small, the (011) plane does not become the specific crystal growth plane in some cases. Further, as for the lower alcohol, it is preferable to use alcohol having a number of carbon atoms of 2 to 4. It is possible to preferably exemplify, for example, ethanol, isopropyl alcohol, and n-butanol. It is also possible to appropriately add diethyl ether and/or diisopropyl ether to regulate the solubility. Two or more alcohols, which are selected from the alcohols as described above, can be mixed and used as a solvent for recrystallization as well. The alcohol as described above may be used together with water when the alcohol is used, or the alcohol may be used in a state in which water is previously contained. It is preferable to adopt such a form that water is added as the poor solvent after the dissolution of the crystal.

Recrystallization can be performed in accordance with any ordinary recrystallization technique.

Figure 1:
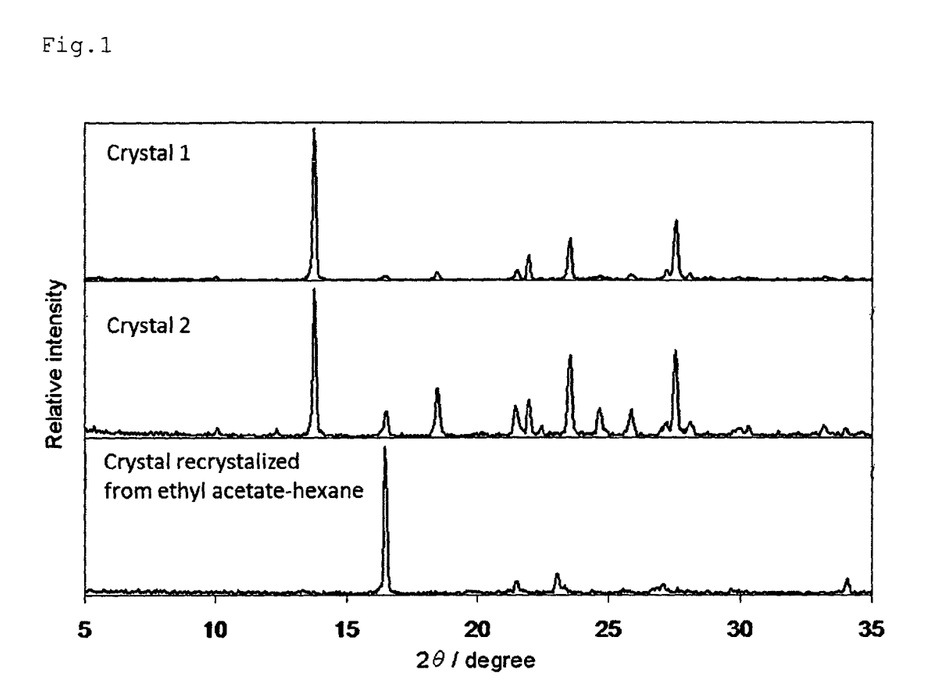
FIG. 1 shows results of the powder X-ray diffraction measurements performed for Crystal 1 of Example 1, Crystal 2 of Example 2, and a crystal having such a crystal habit that the (11-1) plane is a specific crystal growth plane.

Those having crystal habits are not known in relation to the crystals of luliconazole. However, the present inventors have grasped that various crystals having different characteristics are obtained depending on the difference in the step of producing the crystal, for example, depending on the difference in the recrystallization solvent and the recrystallization method. In order to elucidate the cause thereof, the present inventors performed the recrystallization while changing the recrystallization solvent and the recrystallization method, and the present inventors performed the powder X-ray diffraction measurement. In relation thereto, FIG. 1 shows the result of the powder X-ray diffraction measurements performed for the crystals having such a crystal habit that the (011) plane is the specific crystal growth plane. It has been acknowledged that the value of the diffraction angle 2θ of the diffraction peak corresponding to the (011) plane is provided in the vicinity of 13.5°. It has been acknowledged that any diffraction peak is present at this position during the investigation of the luliconazole crystal having been hitherto performed by the present inventors. However, this diffraction peak has never appeared in a strong intensity. It has been judged that a novel crystal habit has been found out.

The crystal, which has such a crystal habit that the (011) plane is the specific crystal growth plane as described above, has the crystal system which resides in the monoclinic crystal. On the other hand, the crystal, which has such a crystal habit that the (11-1) plane is the specific crystal growth plane and which is obtained by recrystallizing luliconazole from a mixed solvent obtained by mixing equal amounts of ethyl acetate and normal hexane, also has the crystal system which resides in the monoclinic crystal, wherein the diffraction angle, which is obtained as a result of the powder X-ray diffraction measurement, is coincident with that of the crystal which has such a crystal habit that the (011) plane is the specific crystal growth plane. However, the diffraction intensity differs between the both. That is, it is considered that the two types of crystals described above have the same crystal form but have different crystal habits.

The specific crystal growth plane of the crystal herein means the plane on which the growth occurs with ease as compared with other planes. The specific crystal growth plane is the plane which belongs to the peak that has a significantly strong intensity as compared with integrated intensities of other diffraction peaks within a measured diffraction angle range when the powder X-ray diffraction measurement is performed. The specific crystal growth plane of the crystal can be detected, for example, as the peak which specifically has the high diffraction intensity in the powder X-ray diffraction measurements for the crystals.

In this context, the phrase "the value of 2θ is provided in the vicinity of 13.5°" means, for example, that 2θ is provided in a range of 13.5°±0.7°, preferably that 2θ is provided in 13.5°±0.5°.

The crystal of the present invention is characterized in that the diffraction peak, which is provided in the vicinity of 2θ=13.5°, is specifically large. The phrase "the diffraction peak, which is provided in the vicinity of 2θ=13.5°, is specifically large" means that "the integrated intensity of the diffraction peak provided in the vicinity of 13.5° is not less than ¼ of the sum total of the integrated intensities of all of the diffraction peaks, i.e., not less than 25%, in relation to the integrated intensity ratio concerning the diffraction peaks detected in a range of 2θ=5 to 35° in the powder X-ray diffraction pattern". The numerical value is presented with reference to the effect of the crystal referred to in Examples described later on.

In another viewpoint, the phrase "the diffraction peak, which is provided in the vicinity of 2θ=13.5°, is specifically large" may mean that "$I_{(011)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than ¼, provided that integrated intensities of diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35°".

Luliconazole, which is to be used to prepare the crystal having the crystal habit as described above, can be used irrelevant to the crystal system thereof, provided that the purity thereof is not less than 90% and more preferably not less than 95%. Luliconazole as described above can be synthesized, for example, in accordance with a method described in Japanese Patent Application Laid-open No. 60-218387. That is, 1-(cyanomethyl)imidazole and carbon disulfide are reacted to obtain a compound of (III) which is reacted with a compound of a general formula (II) having a leaving group, and thus a compound represented by a certain general formula (1) can be obtained. The compound, which corresponds to R=X=Cl and which is included in the compounds represented by the general formula (1), is luliconazole. The leaving group as described above can be preferably exemplified, for example, by methanesulfonyloxy group, benzenesulfonyloxy group, p-toluenesulfonyloxy group, or halogen atom.

In the formulas, Y and Y' represent leaving groups, and M represents alkali metal.

(2) Active Pharmaceutical Ingredient of the Present Invention

The crystal, which is the crystal of the present invention obtained as described above and which has such a crystal habit that the (011) plane is the specific crystal growth plane, is excellent in the solubility in alcohol, especially ethanol. The crystal of the present invention is excellent in the function to avoid any remaining crystal which is usually fine or minute and which cannot be sensed by naked eyes. Therefore, even when the filtration is performed by using a filter paper for sterilization having a small pore size, any slight decrease in the active ingredient, which would be otherwise caused thereby, is not observed. Therefore, the crystal of the present invention is preferred as the active ingredient for the pharmaceutical preparation (medicament preparation) to be produced in accordance with the production method including the sterilizing filtration (sterilization filtration) step. The pharmaceutical preparation (medicament preparation) as described above can be preferably exemplified, for example, by injections (injectable medicines) which are directed to vaginitis and pneumonia. It is a matter of course that the characteristic as described above scarcely causes any inconvenience or disadvantage even when the crystal of the present invention is applied to any other pharmaceutical preparation (medicament preparation). Therefore, the crystal of the present invention can be used, for example, for therapeutic agents for trichophytosis. This feature may be further described as follows. That is, the treatment or process, in which fine or minute undissolved matters are removed by means of a pore size of 0.2 to 0.5 μm, is advantageous in order to improve the time-dependent stability as well. In view of the fact as described above, the crystal of the present invention can be used as an active pharmaceutical ingredient. This material is the active pharmaceutical ingredient of the present invention.

The active pharmaceutical ingredient of the present invention can contain substances, impurities, and analogs within a range as permitted in relation to the active pharmaceutical ingredient, other than the crystal of luliconazole. However, it is especially preferable to adopt a form consisting essentially of the crystal of luliconazole.

<Diffraction Peak in Vicinity of 2θ=13.5° in Powder X-Ray Diffraction Pattern>

The crystal habit of the crystal of the present invention is characterized by the diffraction peak existing in the vicinity of 2θ=13.5° in the powder X-ray diffraction pattern. The diffraction peak of 2θ=13.5° in the powder X-ray diffraction pattern has been theoretically calculated according to the single crystal (monocrystal) X-ray structure analysis data. As a result, the diffraction peak represents the (011) plane. Two sulfur atoms are arranged on this plane. On the contrary, in the case of another crystal which is a conventionally known crystal and which is recrystallized from n-hexane-ethyl acetate, the crystal has such a crystal habit that the (11-1) plane is the specific crystal growth plane, wherein phenyl group is arranged on this plane. This plane is the plane which is represented by the diffraction peak existing in the vicinity of 2θ=16° in the powder X-ray diffraction pattern.

(3) Pharmaceutical Composition of the Present Invention

The pharmaceutical composition of the present invention is characterized in that the pharmaceutical composition contains the crystal of the present invention or the active pharmaceutical ingredient of the present invention described above. The crystal as described above is excellent in the solubility in lower alcohol such as ethanol or the like, wherein fine or minute crystals, which are hardly sensed by naked eyes, scarcely remain in the dissolving step. In relation thereto, the fine crystals as described above are removed in the step of performing the filtration, especially the sterilizing filtration with a pore size of 0.2 μm to 0.5 μm. However, when the crystal of the present invention is used, any fine crystal as described above does not remain. Therefore, it is possible to avoid the deterioration of the activity corresponding thereto. The activity, which is deteriorated during the process as described above, does not substantially affect the data of MIC or the like. However, any delicate influence is exerted on the threshold value of the efficacy of the medicine. Therefore, it is preferable that the amount of deteriorated activity is small, in view of the purport of the medicine. Further, any remaining fine crystal may induce the crystallization in a time-dependent manner. Therefore, it is preferable that fine or minute crystals are removed in this sense as well. Therefore, it is affirmed that the crystal of the present invention or the active pharmaceutical ingredient of the present invention is useful as the active ingredient for the pharmaceutical preparation which has any possibility to cause the deterioration of the activity as described above, in other words, for the pharmaceutical preparation for which the step of performing the sterilizing filtration is included in the production steps. The content of luliconazole in the pharmaceutical composition of the present invention is preferably 0.1 to 30% by mass and more preferably 0.5 to 15% by mass with respect to the total amount of the pharmaceutical composition.

The pharmaceutical preparation of the present invention can be produced by performing the process or treatment in accordance with any ordinary method while appropriately adding thereto, for example, solvent, coloring agent, antioxidant, chelating agent, emulsifier/dispersing agent, solubilizing agent, disintegrating agent, excipient, binding agent, coating agent, and taste/odor-correcting agent other than the luliconazole crystal having such a crystal habit that the (011) plane is the specific crystal growth plane.

The pharmaceutical composition of the present invention is preferably used to treat or cure the disease caused by any fungus or prevent the deterioration of the disease by utilizing the characteristic of luliconazole. The disease caused by any fungus can be exemplified by *tinea pedis* such as athlete's foot, *tinea corporis* such as candidiasis and *tinea versicolor*, and trichophytosis of hard keratin portion such as *tinea unguium*. It is especially preferable to use the pharmaceutical composition of the present invention for treating the disease of the hard keratin portion such as *tinea unguium*, because the effect thereof is remarkable. The effect of the pharmaceutical composition of the present invention is expressed on the nail especially preferably. However, the effect is also exerted on any ordinary dermatomycosis. Therefore, the pharmaceutical composition, which is directed to the dermatomycosis and which fulfills the construction of the present invention, also belongs to the technical scope of the present invention. The dermatomycosis as described above can be exemplified, for example, by the *tinea pedis* and the trichophytosis of the propagation in horny substance type, the trichophytosis of the propagation in horny substance type appearing, for example, in the heel and being included in the *tinea pedis*. As for the dermatomycosis described above, it is preferable to make the application to the trichophytosis of the propagation in horny substance type on which any ordinary agent or drug hardly exerts the effect, because the effect of the present invention remarkably arises. Further, it is also possible to preferably exemplify, for example, the application to vaginitis (colpitis) and pneumonia caused, for example, by *Candida* or *Trichomonas*, the percutaneous administration to outer labia, the intravaginal administration, the oral administration, and the administration by injection. In the case of the administration against *Candida* or *Trichomonas* as described above, it is possible to especially preferably exemplify the administration to outer labia.

The mode of use can be appropriately selected while considering, for example, the body weight, the age, the sexuality, and the symptoms or condition of the patient. However, in the case of an adult, it is preferable to administer luliconazole in an amount of 0.01 to 5 g per day in ordinary cases. Reference can be made to the amount of use of luliconazole ordinarily used for the disease caused by any fungus. In the case of any disease caused by *Trichomonas* or the like, luliconazole is also used in accordance therewith.

For example, in the case of any preparation for external use, it is possible to exemplify the application in an appropriate amount to the disease portion once or several times a day. It is preferable that the treatment as described above is performed every day. In the case of any internal medicine (agent), it is preferable to administer 500 mg to 2000 mg once or several times a day. In the case of any vaginal tablet, it is preferable to perform the adjustment so that the amount of luliconazole is 500 to 1500 mg and perform the administration intravaginally once per a day or several days. In the vaginal administration of luliconazole, it is possible to simultaneously treat protozoa such as *Trichomonas* and fungi such as *Candida*, which is preferred. In particular, in the case of the mixed infection (combined infection), the treatment can be performed by using one agent, which is preferred. Further, in the case of vaginitis (colpitis) caused by the simple infection of *Trichomonas*, it is possible to preventively avoid the fungal infection of *Candida* or the like simultaneously with the medical treatment, which is preferred. Further, the effect of the present invention is exerted even when the target microorganism is any fungus. Therefore, the rights or claims of the crystal having the crystal habit and the pharmaceutical composition containing the concerning crystal as the active ingredient of the present invention also encompass the use as the antifungal agent to treat or prevent the simultaneous infection (coinfection) with protozoa as described above.

It is possible to avoid the recurrence and the reinfection as described above by administering the pharmaceutical composition of the present invention for 1 week to 2 weeks after the quietness of symptoms. In such a mode, the pharmaceutical composition of the present invention has the preventive effect.

EXAMPLES

The present invention will be explained in further detail below as exemplified by Examples. However, the present invention is not limited to Examples described below.

Example 1

Figure 2:
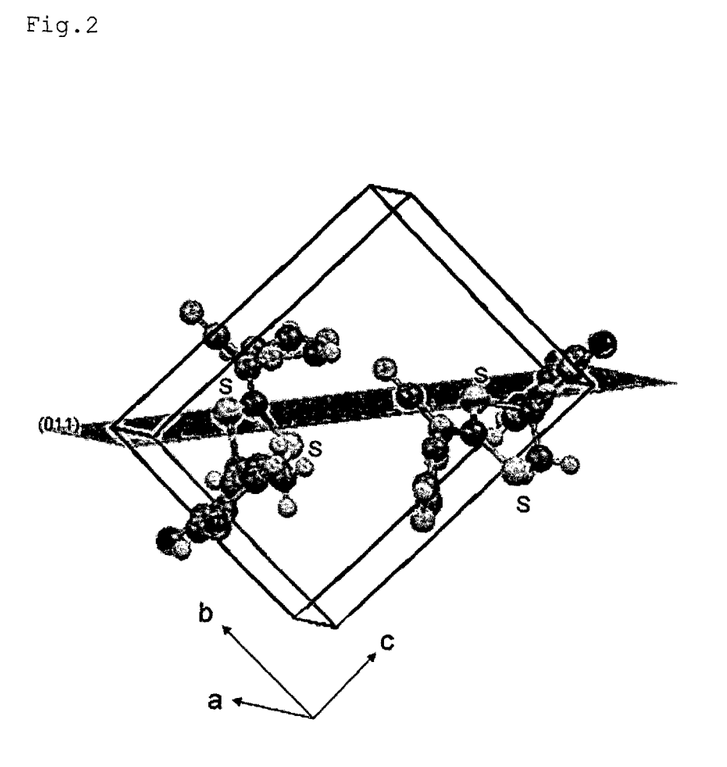
FIG. 2 shows the packing diagram (halftone image) obtained by single crystal X-ray diffraction data of luliconazole for Crystal 1 of Example 1. The atom affixed with a symbol S is the sulfur atom.

150 mL of ethanol was added to 5 g of luliconazole, followed by being refluxed and solubilized. Cooling was performed slowly until arrival at 65° C. while stirring, and this temperature was retained for 10 minutes. After that, 20 mL of water was added thereto, followed by being stirred and cooled. Deposited crystals were collected by filtration, followed by being dried for 48 hours while performing blowing at 30° C. to obtain Crystal 1 of the present invention. A powder X-ray diffraction pattern of Crystal 1 is shown in FIG. 1. The powder X-ray diffraction measurement was performed under the following condition: apparatus: XRD-DSCII produced by Rigaku Corporation, Condition: X-ray source: CuKα, measurement temperature: room temperature, tube voltage: 40 kV, tube current: 40 mA, 2θ: 5 to 35°, step angle: 0.05°. On the basis of the data, it was analyzed that the diffraction peak of 2θ=13.5° of this chart resided in the (011) plane while being collated with the data of the single crystal X-ray structure analysis. Characteristic values obtained by the single crystal X-ray structure analysis were provided as shown in <Single crystal X-ray structure analysis data> described later on. The single crystal X-ray structure analysis was performed under the following condition: apparatus: RU-H2R produced by Rigaku Corporation, Condition: X-ray source: CuKα, measurement temperature: 26° C., tube voltage: 50 kV, tube current: 180 mA, 2θ max: 150.0°, structure analysis method: direct method (SHELX 86). Further, various pieces of data of the single crystal X-ray structure analysis, and the peak area ratio of the (11-1) plane and the peak area ratio of the (011) plane in the powder X-ray diffraction pattern are shown in <Integrated intensity ratio in powder X-ray diffraction measurement> described later on. FIG. 2 shows the crystal structure and the specific crystal growth plane as determined by means of the calculation (name of software: Mercury) from analysis values obtained according to the single crystal X-ray structure analysis.

Crystal of Comparative Example, in which the (11-1) plane was the specific crystal growth plane, was obtained by recrystallizing luliconazole from a mixed solvent obtained by mixing equal amounts of ethyl acetate and normal hexane. In the case of this material, $I_{(11-1)}$ with respect to the sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ was 61%, and $I_{(011)}$ with respect to the same sum total was 2%, provided that integrated intensities of diffraction peaks, which corresponded to the (001), (100), (10-1), (011), (110), (11-1), (10-2), (11-2), (020), (021), (20-2), (121), (013), (11-3), and (221) planes, were designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35°.

<Single Crystal X-Ray Structure Analysis Data>
Crystal System: Monoclinic Crystal
Space group: $P2_1$
Lattice Constant:
a=9.0171(9) Å
b=8.167(1) Å
c=10.878(1) Å
β=95.917(9) °
R Factor:
R=0.046
$R_w$=0.047

<Integrated Intensity Ratio in Powder X-Ray Diffraction Measurement>

$I_{(011)}$ with respect to the sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ was 54%, and $I_{(11-1)}$ with respect to the same sum total was 2%, provided that integrated intensities of diffraction peaks, which corresponded to the (001), (100), (10-1), (011), (110), (11-1), (10-2), (11-2), (020), (021), (20-2), (121), (013), (11-3), and (221) planes, were designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35°.

Example 2

150 mL of ethanol was added to 5 g of luliconazole, followed by being refluxed and solubilized. Cooling was performed slowly until arrival at 70° C. while stirring, and this temperature was retained for 10 minutes. 15 mL of water was added thereto, followed by being stirred and cooled. Deposited crystals were collected by filtration, followed by being dried for 48 hours while performing blowing at 30° C. to obtain Crystal 2 of the present invention. A powder X-ray diffraction pattern of Crystal 2 is shown in FIG. 1.

Characteristic values obtained by the single crystal X-ray structure analysis were as follows. Further, various pieces of data of the single crystal X-ray structure analysis, and the peak area ratio of the (11-1) plane and the peak area ratio of the (011) plane in the powder X-ray diffraction pattern are shown below.

The powder X-ray diffraction measurement and the single crystal X-ray structure analysis were performed in the same manner as in Example 1.

<Single Crystal X-Ray Structure Analysis Data>
Crystal system: monoclinic crystal
Space group: $P2_1$
Lattice Constant:
a=9.0171(9) Å
b=8.167 (1) Å
c=10.878(1) Å
β=95.917(9)°
R Factor:
R=0.046
$R_w$=0.047

<Integrated Intensity Ratio in Powder X-Ray Diffraction Measurement>

$I_{(011)}$ with respect to the sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ was 26%, and $I_{(11-1)}$ with respect to the same sum total was 5%, provided that integrated intensities of diffraction peaks, which corresponded to the (001), (100), (10-1), (011), (110), (11-1), (10-2), (11-2), (020), (021), (20-2), (121), (013), (11-3), and (221) planes, were designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35°.

Example 3

The effect on *Trichomonas vaginalis* (clinically isolated strain) of the crystal was investigated while being compared with a crystal having such a crystal habit that the (11-1) plane was the specific crystal growth plane. A solution of 10% ethanol/physiological saline was used as a control.

Crystal of Comparative Example described above was used as the crystal which had such a crystal habit that the (11-1) plane was the specific crystal growth plane. Crystal 2 was used as the crystal which had such a crystal habit that the (011) plane was the specific crystal growth plane.

Each of the crystals of luliconazole was weighed in an amount of 7.02 mg to which 10 mL of ethanol was added to dissolve the crystal. After confirming the absence of the crystal by visual observation, 100 μL of the solution was used as an aliquot, and 900 μL of physiological saline was added thereto. The resultant solution was subjected to the sterilizing filtration by using a filter having a pore size of 0.22 μm to provide a sample of 5.02 μg/mL (final concentration). 250 μL of an aliquot was taken therefrom, to which 250 μL of 10% ethanol/physiological saline was added to provide a sample of 2.51 μg/mL (final concentration).

0.5 mL of each of the samples was added to "*Trichomonas* medium F" (produced by Fuji Pharma Co., Ltd.), and 100 μL of *Trichomonas* culture (5×10³ individuals of *Trichomonas*)

was added thereto, followed by being cultured for 96 hours. After performing cooling for 10 minutes in ice water, the medium was stirred, which was spread on a hemocytometer to count a number of survived individuals of *Trichomonas*. As for a control, 0.5 mL of 10% ethanol/physiological saline was added in place of the sample. Results are shown in Table 1. Accordingly, it is appreciated that MIC is almost unchanged, but Crystal 2 is significantly excellent in the suppression of the growth of *Trichomonas* in the vicinity of MIC as compared with the crystal having such a crystal habit that the (11-1) plane is the specific crystal growth plane. Further, according to the fact that the peak area ratio of the (011) plane was 26%, it is possible to estimate and acknowledge that the effect as described above is provided if $I_{(011)}$ with respect to the sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than 25%, provided that integrated intensities of diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35° in a powder X-ray diffraction pattern in which CuKα is used as an X-ray source.

TABLE 1

| Sample | | Number of survived individuals of *Trichomonas* (individuals/mL) |
|---|---|---|
| Crystal 2 | 5.02 µg/mL | 23333 ± 5773 |
|  | 2.51 µg/mL | 23333 ± 5773 |
| Crystal of | 5.02 µg/mL | 23333 ± 5773 |
| Comp. Ex. | 2.51 µg/mL | 116667 ± 15275 |
| Control |  | 60000 ± 10000 |

Example 4

Each of Crystal 1 and Crystal 2 was correctly weighed in an amount of 3.45 mg, which was dissolved in 10 mL of ethanol, in the same manner as in Example 3. After confirming the absence of the crystal by visual observation, 100 µL of the solution was used as an aliquot, and 900 µL of physiological saline was added thereto. The resultant solution was subjected to the sterilizing filtration by using a filter having a pore size of 0.22 to provide a sample or specimen. 0.5 mL of each of the specimens was added to "*Trichomonas* medium F" (produced by Fuji Pharma Co., Ltd.). Further, 100 µL of *Trichomonas* culture, which had been precultured and prepared to give $2.7 \times 10^5$ individuals/mL by adding the medium, was added, followed by being cultured for 72 hours at 37° C. (final concentration: 2.4 µg/mL). After completing the cultivation, the number of survived individuals of *Trichomonas* was counted by using a hemocytometer. Results are shown in Table 2. It is appreciated that Crystal 1, in which the integrated intensity ratio of the diffraction peak corresponding to the (011) plane is 54%, provides the anti-*Trichomonas* effect which is more excellent than that of Crystal 2 in which the integrated intensity ratio of the diffraction peak corresponding to the (011) plane is 26%. Therefore, as for the effect of the present invention, it is estimated and acknowledged that the larger the constitutive ratio of the plane is, the larger the exhibited effect is, in relation to those in which the integrated intensity ratio of the diffraction peak corresponding to the (011) plane is not less than 25%.

TABLE 2

| | Number of survived protozoa (100000 individuals/mL) | |
|---|---|---|
| Final concentration (µg/mL) | Crystal 1 | Crystal 2 |
| 0 | | 7.53 ± 1.01 |
| 2.4 | 5.57 ± 0.42 | 6.57 ± 0.60 |
| 4.8 | 0 | 0 |
| 9.6 | 0 | 0 |

Example 5

An external preparation for skin was manufactured in accordance with the following formulation. That is, formulation components A and B were heated, stirred, and solubilized. After that, the component B was added to the components A, followed by being neutralized, stirred, and cooled. Sterilizing filtration was performed by using a filter having a pore size of 0.32 µm. This preparation is useful to cure or treat *tinea pedis*, candidiasis of outer labia, and trichomoniasis of outer labia.

TABLE 3

| Component | % by mass |
|---|---|
| (A) | |
| Luliconazole (Example 1) | 1 |
| Benzyl alcohol | 1 |
| Crotamiton | 5 |
| Ethanol | 87 |
| Carboxyvinyl polymer | 3 |
| (B) | |
| Triethanolamine | 3 |

INDUSTRIAL APPLICABILITY

The present invention can be applied to the pharmaceutical.

What is claimed is:

1. A crystal of luliconazole represented by the following formula, wherein the crystal is recrystallized from alcohol which may contain water, and the crystal has such a crystal habit that (011) plane is a specific crystal growth plane, and the crystal is characterized by crystal system of monoclinic crystal, space group of $P2_1$, lattice constant of a =9.0171(9) Å, b =8.167(1) Å, c =10.878(1) Å, β=95.917(9) °, R factor of R =0.046, $R_w$ =0.047:

(luliconazole)

2. The crystal according to claim 1, wherein $I_{(011)}$ with respect to a sum total of $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ is not less than 25%, provided that integrated intensities of diffraction peaks, which correspond to the (001), (100), (10-1), (011), (110), (11-1), (10-2), (11-2), (020), (021), (20-2), (121), (013), (11-3), and (221) planes, are designated as $I_{(001)}$, $I_{(100)}$, $I_{(10-1)}$, $I_{(011)}$, $I_{(110)}$, $I_{(11-1)}$, $I_{(10-2)}$, $I_{(11-2)}$, $I_{(020)}$, $I_{(021)}$, $I_{(20-2)}$, $I_{(121)}$, $I_{(013)}$, $I_{(11-3)}$, and $I_{(221)}$ respectively in relation to the diffraction peaks detected in a range of 2θ=5 to 35° in a powder X-ray diffractometry using CuKα radiation.

3. The crystal according to claim 1, wherein the crystal has such a crystal habit that sulfur atom is arranged on a specific crystal growth plane.

4. An active pharmaceutical ingredient, containing the crystal as defined in claim 1.

5. A method for producing a pharmaceutical composition, comprising a step of dissolving, in a solvent, the crystal as defined in claim 1, followed by being filtrated through a sterilizing filter.

6. The method according to claim 5, wherein the sterilizing filter is a filter which has a pore size of 0.2 μm to 0.5 μm.

7. The method according to claim 5, wherein the pharmaceutical composition is a pharmaceutical composition which is usable for vaginitis or pneumonia.

* * * * *